(12) United States Patent
Slepian et al.

(10) Patent No.: US 11,668,699 B2
(45) Date of Patent: Jun. 6, 2023

(54) COMPOSITIONS AND METHODS FOR DETERMINING MECHANICAL PROPERTIES OF CELLS

(71) Applicant: Arizona Board of Regents on Behalf of the University of Arizona, Tucson, AZ (US)

(72) Inventors: Marvin J. Slepian, Tucson, AZ (US); Sui Ling Leung, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 23 days.

(21) Appl. No.: 16/918,352

(22) Filed: Jul. 1, 2020

(65) Prior Publication Data

US 2020/0333319 A1 Oct. 22, 2020

Related U.S. Application Data

(62) Division of application No. 15/488,085, filed on Apr. 14, 2017, now abandoned.

(60) Provisional application No. 62/322,338, filed on Apr. 14, 2016.

(51) Int. Cl.
| | |
|---|---|
| *C12M 3/00* | (2006.01) |
| *B01L 3/00* | (2006.01) |
| *G01N 33/00* | (2006.01) |
| *G01N 33/483* | (2006.01) |
| *G01N 15/10* | (2006.01) |
| *G01N 15/14* | (2006.01) |
| *B03C 5/00* | (2006.01) |
| *B03C 5/02* | (2006.01) |
| *G01N 15/00* | (2006.01) |

(52) U.S. Cl.
CPC .... *G01N 33/4836* (2013.01); *B01L 3/502761* (2013.01); *G01N 15/1031* (2013.01); *G01N 15/1463* (2013.01); *B01L 2200/0663* (2013.01); *B01L 2300/0645* (2013.01); *B01L 2400/0424* (2013.01); *B03C 5/005* (2013.01); *B03C 5/026* (2013.01); *B03C 2201/26* (2013.01); *G01N 2015/0084* (2013.01); *G01N 2015/1006* (2013.01); *G01N 2015/1495* (2013.01)

(58) Field of Classification Search
CPC .................. B01L 2400/0424; C12M 35/02
See application file for complete search history.

(56) References Cited

U.S. PATENT DOCUMENTS

| | | | |
|---|---|---|---|
| 6,653,136 B1 | 11/2003 | Dodgson | |
| 7,553,662 B2 | 6/2009 | El-Haj | |
| 8,499,645 B2 | 8/2013 | Chasiotis | |
| 8,771,933 B2 * | 7/2014 | Han | G01N 33/5008 435/2 |

(Continued)

OTHER PUBLICATIONS

Bakewell, D.V.-I., N.; Holmes, D., Dielectrophoresis of Biomolecules. JSM Nanotechnology & Nanomedicine, 2013. 1(1003): p. 1-14.

(Continued)

*Primary Examiner* — Nathan A Bowers
(74) *Attorney, Agent, or Firm* — Casimir Jones, S.C.; Tanya A. Arenson

(57) ABSTRACT

Provided herein are systems and method for measuring cell stiffness. In particular, provided herein are microelectrode configuration and systems for measuring platelet deformation and stiffness.

12 Claims, 6 Drawing Sheets

(56) References Cited

U.S. PATENT DOCUMENTS

| | | | |
|---|---|---|---|
| 8,935,098 | B2 | 1/2015 | Di Carlo |
| 9,074,978 | B2 | 7/2015 | Lo |
| 9,134,294 | B2 | 9/2015 | Manalis |
| 9,250,113 | B2 | 2/2016 | Bashir |
| 2010/0006441 | A1* | 1/2010 | Renaud ............. B01L 3/502746 204/643 |
| 2014/0247971 | A1* | 9/2014 | Bharadwaj ........... G02B 21/365 382/133 |
| 2017/0016858 | A1 | 1/2017 | Kobayashi |
| 2017/0342480 | A1 | 11/2017 | Astier |
| 2018/0111124 | A1 | 4/2018 | Anand |
| 2018/0216180 | A1 | 8/2018 | Lee |

OTHER PUBLICATIONS

Berger, G., D.W. Hartwell, and D.D. Wagner, P-Selectin and platelet clearance. Blood, 1998. 92(11): p. 4446-52.

Berman, C.L., et al., A Platelet Alpha Granule Membrane-Protein That is Associated with the Plasma-Membrane after Activation—Characterization and Subcellular-Localization of Platelet Activation-Dependent Granule-External Membrane-Protein. Journal of Clinical Investigation, 1986. 78(1): p. 130-137.

Bluestein, D., et al., Device thrombogenicity emulation: A novel methodology for optimizing the thromboresistance of cardiovascular devices (vol. 46, p. 334, 2012). Journal of Biomechanics, 2013. 46(7): p. 1413-1413.

Burt, J.P.H., R. Pethig, and M.S. Talary, Microelectrode devices for manipulating and analysing bioparticles. Transactions of the Institute of Measurement and Control, 1998. 20(2): p. 82-90.

Chen, J., et al., Electrodeformation for Single Cell Mechanical Characterization. 2011 Ieee 24th International Conference on Micro Electro Mechanical Systems (Mems), 2011: p. 1119-1122.

Dos Santos and Rodrigues, Correlation between fracture toughness, work of fracture and fractal dimensions of Alumina-mullite-zirconia composites. Materials Research, 2003. 6(2): p. 219-226.

Gao, J., et al., Hybrid electrokinetic manipulation in high-conductivity media. Lab on a Chip, 2011. 11(10): p. 1770-1775.

GHARIB Effects of membrane stiffening on focal-adhesion bonding under steady and unsteady conditions, in Bio Micro and Nanosystems Conference, 2006, 85, BMN'06. 2006. IEEE Abstract.

Guck, J., et al., Optical deformability as an inherent cell marker for testing malignant transformation and metastatic competence. Biophys J, 2005. 88(5): p. 3689-9).

Guo, Q., S. Park, and H.S. Ma, Microfluidic micropipette aspiration for measuring the deformability of single cells. Lab on a Chip, 2012. 12(15): p. 2687-2695.

Haga, J.H., et al., Quantification of the passive mechanical properties of the resting platelet. Ann Biomed Eng, 1998. 26(2): p. 268-77.

Haghi, M.T., D.; Wood, L. G.; Oliver, B.; Young, p. M.; Chrzanowski, W., A "soft spot" for drug transport: modulation of cell stiffness using fatty acids and its impact on drug transport in lung model. Journal of Materials Chemistry B, 2015. 3: p. 2583-2589.

Hou, H.W., et al., Deformability based cell margination—A simple microfluidic design for malarial infected red blood cell filtration. 6th World Congress of Biomechanics (Web 2010), Pts 1-3, 2010. 31: p. 1671-1674.

Hsu Lin, S.C., et al., A Platelet Membrane-Protein Expressed during Platelet Activation and Secretion—Studies Using a Monoclonal-Antibody Specific for Thrombin-Activated Platelets. Journal of Biological Chemistry, 1984. 259(14): p. 9121-9126.

Hu, X.Y., et al., Marker-specific sorting of rare cells using dielectrophoresis. Proceedings of the National Academy of Sciences of the United States of America, 2005. 102(44): p. 15757-15761.

Jesty and Bluestein, Acetylated prothrombin as a substrate in the measurement of the procoagulant activity of platelets: Elimination of the feedback activation of platelets by thrombin. Analytical Biochemistry, 1999. 272(1): p. 64-70.

Kapoor, Platelet activation and atherothrombosis. New England Journal of Medicine, 2008. 358(15): p. 1638-1638.

Koay, E.J., A.C. Shieh, and K.A. Athanasiou, Creep indentation of single cells. Journal of Biomechanical Engineering-Transactions of the Asme, 2003. 125(3): p. 334-341.

Lee, S.W., et al., Development of microelectrode arrays for artificial retinal implants using liquid crystal polymers. Invest Ophthalmol Vis Sci, 2009. 50(12): p. 5859-66.

Leung, S.L., et al., Gold nano-particle-based thermal sensors fabricated using microspotting and DEP techniques. Sensors and Actuators a-Physical, 2012. 178: p. 32-39.

Lim, C.T., E.H. Zhou, and S.T. Quek, Mechanical models for living cells—A review. Journal of Biomechanics, 2006. 39(2): p. 195-216.

Lincoln, B., et al., Deformability-based flow cytometry. Cytometry Part A, 2004. 59A(2): p. 203-209.

Martinez, E.J., Y. Lanir, and S. Einav, Effects of contact-induced membrane stiffening on platelet adhesion. Biomech Model Mechanobiol, 2004. 2(3): p. 157-67.

Maugis, D. and M. Barquins, Fracture Mechanics and Adherence of Viscoelastic Bodies. Journal of Physics D-Applied Physics, 1978. 11(14): p. 1989.

Morgan, H., M.P. Hughes, and N.G. Green, Separation of submicron bioparticles by dielectrophoresis. Biophys J, 1999. 77(1): p. 516-25.

Neuman, K.C. and A. Nagy, Single-molecule force spectroscopy: optical tweezers, magnetic tweezers and atomic force microscopy. Nature Methods, 2008. 5(6): p. 491-505.

Pasqua, A., et al., Large-scale simulations of fluctuating biological membranes. Journal of Chemical Physics, 2010. 132(15): p. 15410.

Pohi, H.A. and I. Hawk, Separation of living and dead cells by dielectrophoresis. Science, 1966. 152(3722): p. 647.

Pohl, H.A. and U.S. Crane, Dielectrophoresis of Cells. Biophysical Journal, 1971.11(9): p. 711.

Pohl, H.A., The Motion and Precipitation of Suspensoids in Divergent Electric Fields. Journal of Applied Physics, 1951. 22(7): p. 869-871.

Pommer, M.S., et al., Dielectrophoretic separation of platelets from diluted whole blood in microfluidic channels. Electrophoresis, 2008. 29(6): p. 1213-8.

Radmacher, M., et al., Measuring the viscoelastic properties of human platelets with the atomic force microscope. Biophys J, 1996. 70(1): p. 556-67.

Ramos, A., et al., Ac electrokinetics: a review offerees in microelectrode structures. Journal of Physics D-Applied Physics, 1998. 31(18): p. 2338-2353.

Rand, R.P., Mechanical Properties of the Red Cell Membrane. Ii. Viscoelastic Breakdown of the Membrane. Biophys J, 1964. 4: p. 303-16.

Ritchie, Robert O, M.J.B., and Paul Hansma, Plasticity and toughness in bone. Physics Today, 2009. 62(2): p. 41-47).

Sheriff, J., et al., High-shear stress sensitizes platelets to subsequent low-shear conditions. Ann Biomed Eng, 2010. 38(4): p. 1442-50.

Sims, P. J., et al., Complement proteins C5b-9 cause release of membrane vesicles from the platelet surface that are enriched in the membrane receptor for coagulation factor Va and express prothrombinase activity. J Biol Chem, 1988. 263(34): p. 18205-12.

Sun, M., et al., The effect of cellular cholesterol on membrane-cytoskeleton adhesion. J Cell Sci, 2007. 120(Pt 13): p. 2223-31.

Van Vliet, K.J., G. Bao, and S. Suresh, The biomechanics toolbox: experimental approaches for living cells and biomolecules. Acta Materialia, 2003. 51(19): p. 5881-5905.

Vieira-De-Abreu, A., et al., Platelets: versatile effector cells in hemostasis, inflammation, and the immune continuum. Seminars in Immunopathology, 2012. 34(1): p. 5-30).

Wang, X.B., et al., Dielectrophoretic manipulation of particles. Ieee Transactions on Industry Applications, 1997. 33(3): p. 660-669.

Wang, X.J., X.B. Wang, and P.R.C. Gascoyne, General expressions for dielectrophoretic force and electrorotational torque derived using the Maxwell stress tensor method. Journal of Electrostatics, 1997. 39(4): p. 277-295.

Ward, M.D. and D.A. Hammer, Atheoretical analysis for the effect of focal contact formation on cell-substrate attachment strength. Biophys J, 1993. 64(3): p. 936-59.

Yamaguchi, J., et al., Desensitization of DMSO-treated platelets to common agonists via membrane modulation (598.5. Faseb Journal, 2014. 28(1) Abstract.

(56) References Cited

OTHER PUBLICATIONS

Zhang, C., et al., Dielectrophoresis for manipulation of micro/nano particles in microfluidic systems. Anal Bioanal Chem, 2010. 396(1): p. 401-20.
Zhang, J., et al., Nanosecond pulse electric field (nanopulse): a novel non-ligand agonist for platelet activation. Arch Biochem Biophys, 2008. 471(2): p. 240-8.
Zhang, P., et al., Multiscale Particle-Based Modeling of Flowing Platelets in Blood Plasma Using Dissipative Particle Dynamics and Coarse Grained Molecular Dynamics. Cellular and Molecular Bioengineering, 2014. 7(4): p. 552-574.

\* cited by examiner

FIG. 1A
(A)
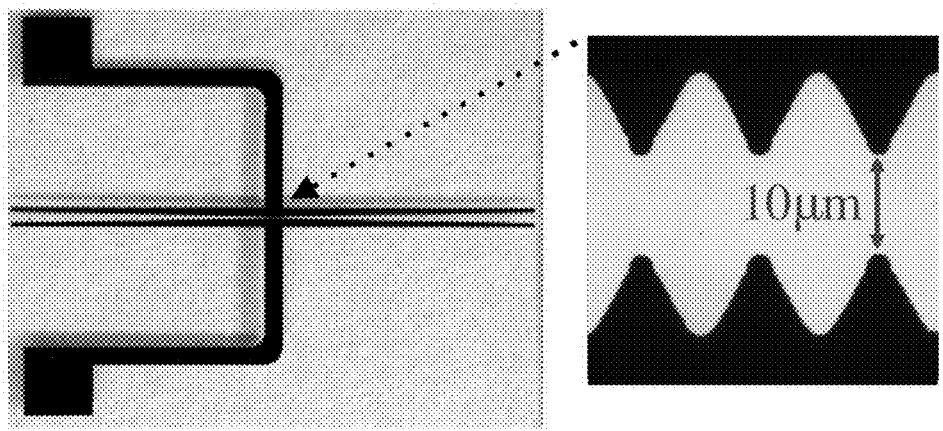
(B)
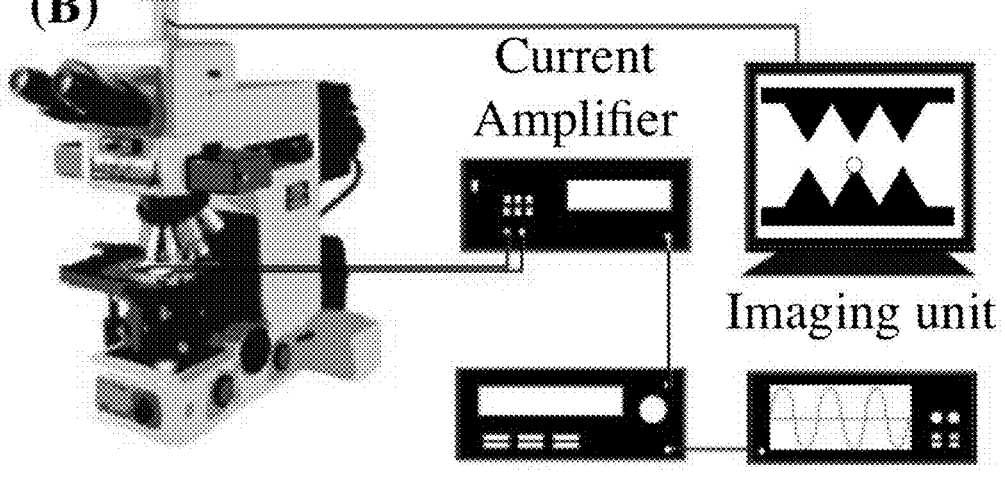
Microscope with electrodes chip    AC signal generator    Cathode ray oscilloscope
FIG. 1B FIG. 2A            FIG. 2B            FIG. 2C
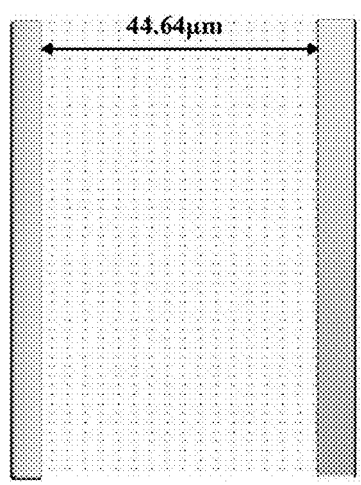 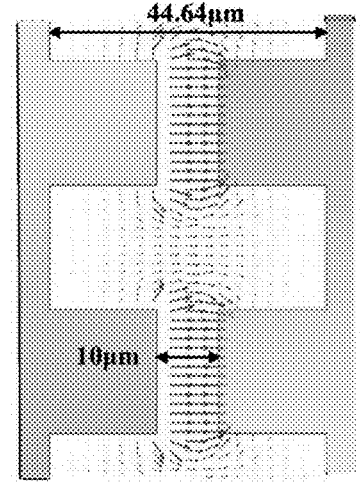 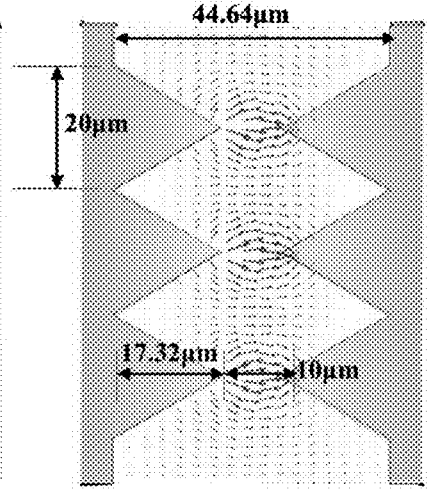
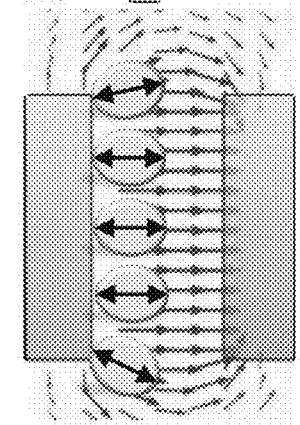 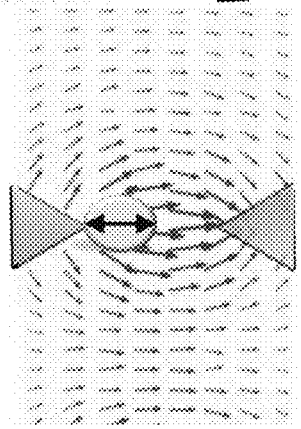
FIG. 2D            FIG. 2E FIG. 3A
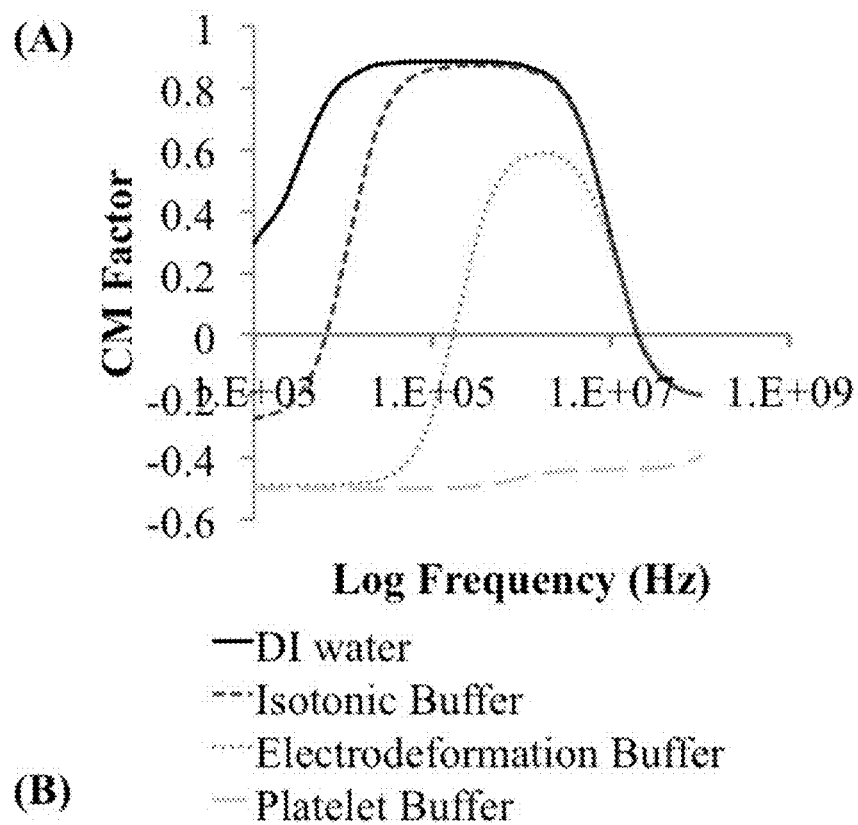
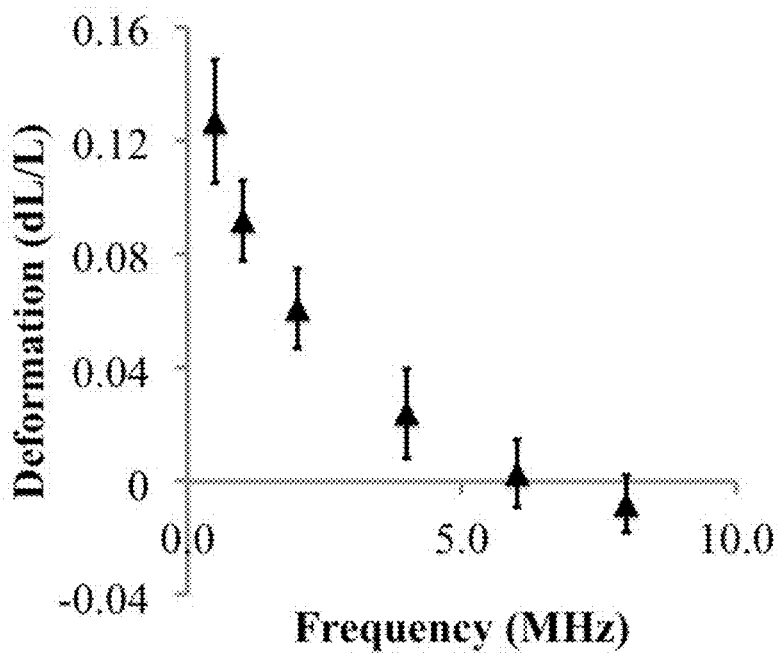
FIG. 3B FIG. 4A
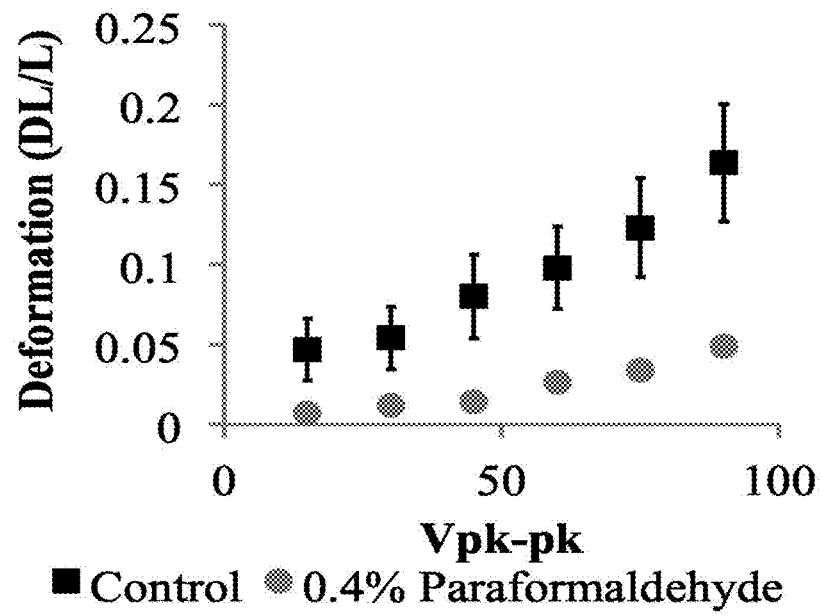
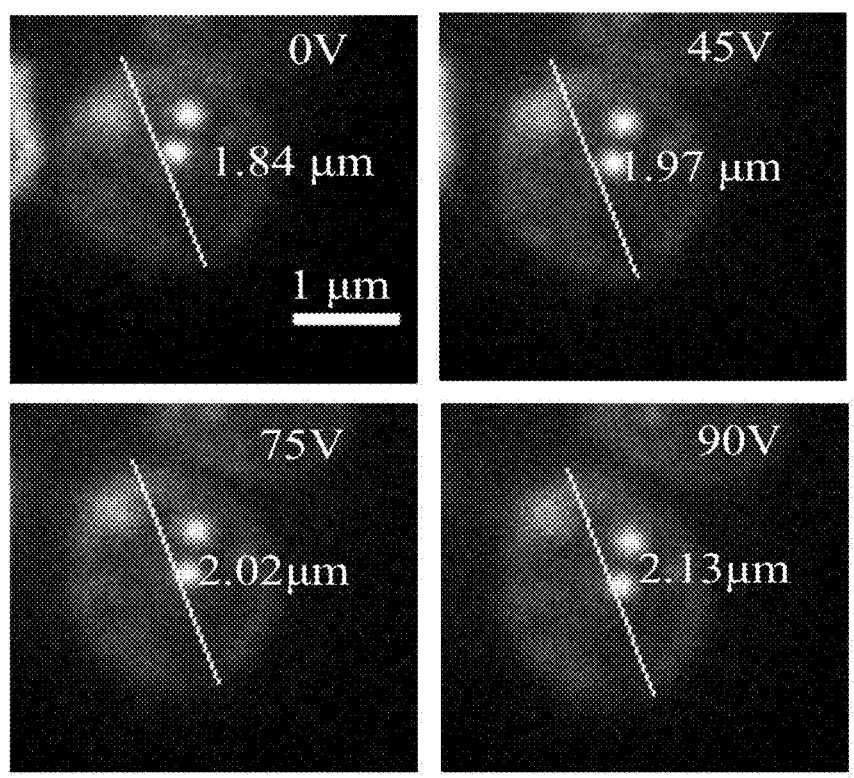
FIG. 4B FIG. 5A
(A)
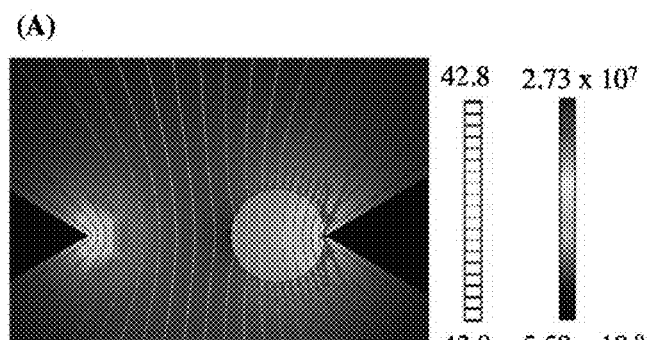
FIG. 5B
(B)
| Electric Field Strength (V/μm) | Time Averaged Electromagnetic Force in x-direction (N) |
|---|---|
| 1.5 | 1.25E-10 |
| 3 | 5.01E-10 |
| 4.5 | 1.13E-09 |
| 6 | 2.01E-09 |
| 7.5 | 3.13E-09 |
| 9 | 4.5E-09 |
FIG. 5C
(C)
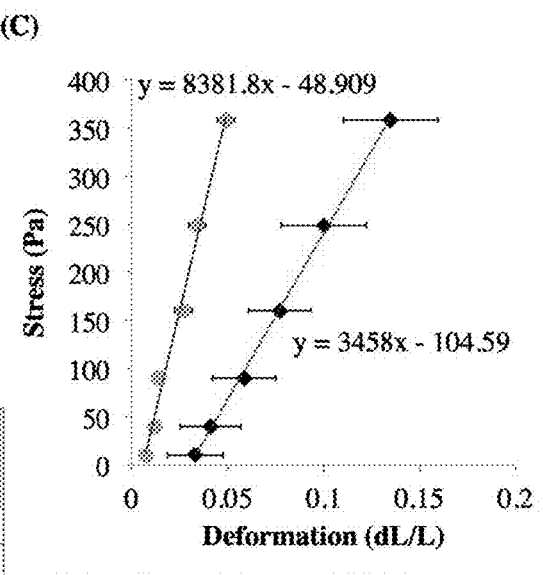
○ Experimental data - 0.4% PFA
◆ Experimental data - Control
—— Linear (Experimental data - 0.4% PFA)
—— Linear (Experimental data - Control)

FIG. 6A
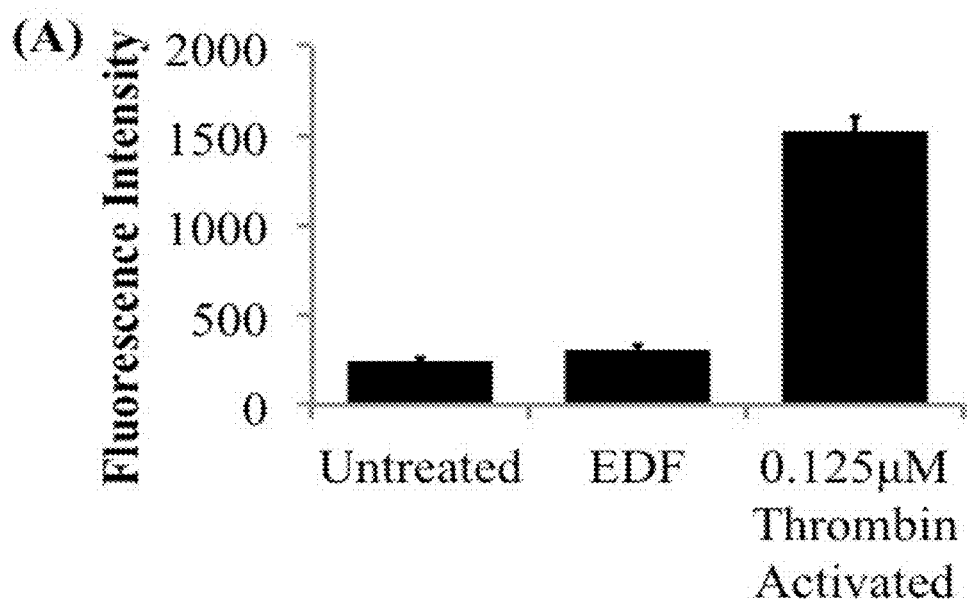
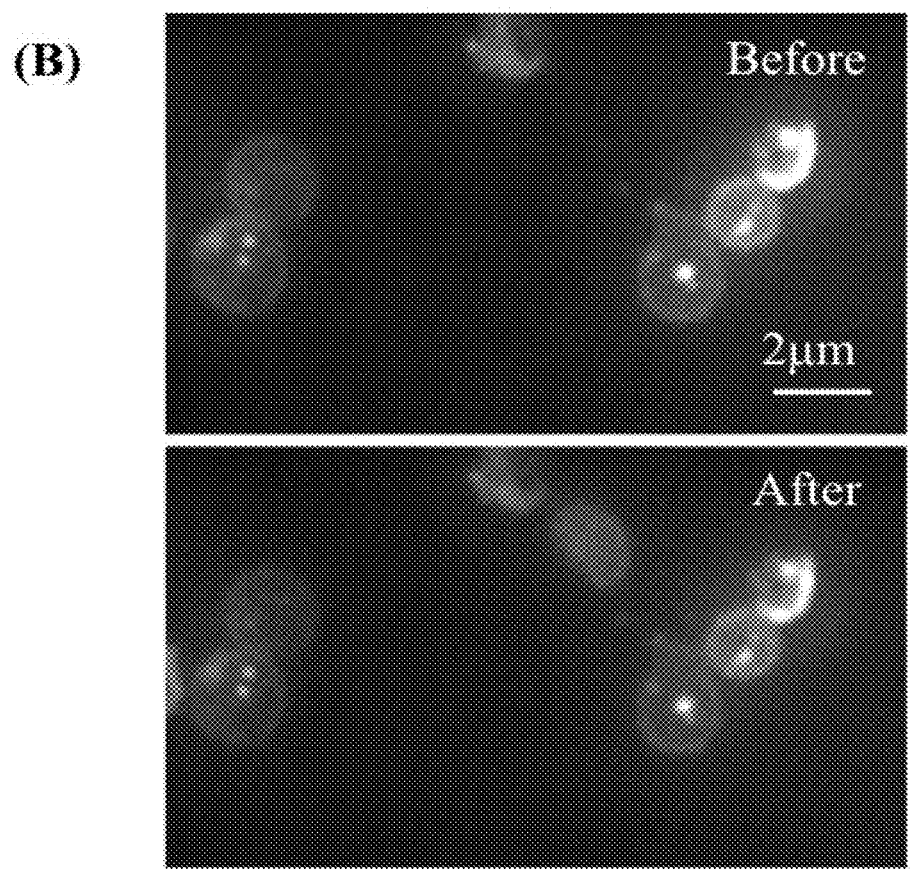
FIG. 6B

COMPOSITIONS AND METHODS FOR DETERMINING MECHANICAL PROPERTIES OF CELLS

PROPERTIES OF CELLS

This application is a divisional of U.S. patent application Ser. No. 15/488,085, filed Apr. 14, 2017, which claims the benefit of U.S. provisional application Ser. No. 62/322,338, filed Apr. 14, 2016, which are incorporated herein by reference in their entireties.

FIELD

Provided herein are systems and methods for measuring mechanical properties of cell or cell component or fragments. In particular, provided herein are microelectrode configuration and systems for measuring platelet deformation and stiffness.

BACKGROUND

Mechanical properties (e.g., stiffness) play a major role in determining mechanical limitations of viscoelastic materials. When subjected to an external load, viscoelastic materials typically store the majority of the input energy through deformation, while partially releasing energy as heat (Ferry, J. D., *Viscoelastic properties of polymers*. 1961, New York: Wiley. 482 p.). As input energy increases, and the ability of a given material to store energy is exceeded, materials begin to crack and fracture (Maugis, D. and M. Barquins, *Fracture Mechanics and Adherence of Viscoelastic Bodies*. Journal of Physics D-Applied Physics, 1978. 11(14): p. 1989; Robert O. Ritchie, M. J. B., and Paul Hansma, Plasticity and toughness in bone. Physics Today, 2009. 62(2): p. 41-47). As such, in mechanics, based on the Griffith-Irwin concept, this critical elastic energy release rate is inversely proportional to material stiffness (Rodrigues, S.F.d.S.J.d.A., *Correlation between fracture toughness, work of fracture and fractal dimensions of Alumina-mullite-zirconia composites*. Materials Research, 2003. 6(2): p. 219-226). Similar mechanical behavior applies to many natural materials, cells, cell components and cell fragments (Rand, R. P., *Mechanical Properties of the Red Cell Membrane. Ii. Viscoelastic Breakdown of the Membrane*. Biophys J, 1964. 4: p. 303-16; Sheriff, J., et al., *High-shear stress sensitizes platelets to subsequent low-shear conditions*. Ann Biomed Eng, 2010. 38(4): p. 1442-50; Guck, J., et al., *Optical deformability as an inherent cell marker for testing malignant transformation and metastatic competence*. Biophys J, 2005. 88(5): p. 3689-9). By way of example, platelets, as an example of a cell or cellular fragment or element, when subjected to mechanical deformation via shear, reach a point where the ability of their membrane to withstand and store energy is exceeded, leading to shape change and fragmentation, with resultant platelet activation and initiation of thrombosis (Rand et al., supra; Sheriff et al., supra).

Platelet activation is a two-edge sword—essential to limit bleeding and repair wounds (Vieira-de-Abreu, A., et al., *Platelets: versatile effector cells in hemostasis, inflammation, and the immune continuum*. Seminars in Immunopathology, 2012. 34(1): p. 5-30) while undesired or inadvertent platelet activation, as occurs with blood passage through atherosclerotic stenotic arteries, diseased valves or therapeutic devices (e.g., ventricular assist devices, mechanical heart valves and stents), results in thrombus formation, reduced blood flow, tissue ischemia, infarction and possible death (Kapoor, J. R., Platelet activation and atherothrombosis. New England Journal of Medicine, 2008. 358(15): p. 1638-1638; Bluestein, D., et al., *Device thrombogenicity emulation: A novel methodology for optimizing the thromboresistance of cardiovascular devices* (vol 46, pg 334, 2012). Journal of Biomechanics, 2013. 46(7): p. 1413-1413). While numerous agents exist to pharmacologically limit platelet activation, present agents limit only biochemical activation pathways with little or no effect on shear or other mechanical activation.

What is needed are improved compositions and methods for analyzing cellular properties.

SUMMARY

Provided herein are systems and methods for measuring mechanical properties of cell or cell component or fragments. In particular, provided herein are microelectrode configurations and systems for measuring platelet deformation and stiffness.

For example, in some embodiments, the present disclosure provides a device that induces a dimensional change in a cell, a cell component, or a cell fragment, comprising: a microelectrode chip comprising a plurality of parallel microelectrodes arranged in a triangular tip orientation, wherein said microelectrode is configured to deliver a varying electric field to a cell, a cell component, or a cell fragment. In some embodiments, the varying electrical fields is induced by or applied via oscillations of voltage. In some embodiments, the varying electric field is electric filed oscillations generated by dielectrophoresis. In some embodiments, the device is fabricated by one or more of photolithography, laser ablation or electron beam patterning.

Some embodiments provide a system for measuring mechanical properties of a cell, a cell component, or a cell fragment, comprising: a) a microelectrode chip comprising a plurality of parallel microelectrodes arranged in a triangular tip orientation; b) a power supply; and c) a visualization means (e.g., microscope, camera, or CCD device). In some embodiments, the microelectrode chip further comprises a fluid chamber on top of the chip. In some embodiments, the microelectrode has an electrode gap distance of approximately 10 µm. In some embodiments, the microelectrode has a surface coating of a Ti—Au—Ti sandwich. In some embodiments, the microscope is a bright field microscope. In some embodiments, the system further comprises a digital camera in operable combination with the microscope.

Additional embodiments provide a method, comprising: a) trapping a plurality of cells, cell components, or cell fragments (e.g., non-adherent cells, platelets, white blood cells, red blood cells, circulating tumor cells, bone marrow cells, stem cells, progenitor cells, endothelial progenitor cells, microparticles, mitochondria, golgi, lusosomes, peroxisomes, budded vesiculated, vacuolated, or membrane-containing cellular constituents) in the microelectrode described herein; and b) measuring a mechanical property (e.g., stiffness, deformation, elasticity, or bending) of the cell, cell fragment, or cell component along the axis of maximum extension. In some embodiments, a voltage of 45 to 90 V is applied to the microelectrode. In some embodiments, the magnitude of deformation of said platelets is proportional to platelet stiffness. In some embodiments, the method further comprises the step of contacting the platelet with a test compound (e.g., drug). In some embodiments, platelet stiffness is correlated with platelet activity.

Still further embodiments provide a kit, comprising: a) a microelectrode chip comprising a plurality of parallel microelectrodes arranged in a triangular tip orientation; b) a power supply; and c) a visualization means.

Yet other embodiments provide a point of care system for measuring mechanical properties of a cell, a cell component, of a cell fragment, comprising: a) a microelectrode chip comprising a plurality of parallel microelectrodes arranged in a triangular tip orientation; b) a power supply; and c) a visualization means.

Additional embodiments provide a system for measuring mechanical properties of a cell, a cell component, of a cell fragment, comprising: a) a microfluidic device comprising a microelectrode comprising a plurality of parallel microelectrodes arranged in a triangular tip orientation; b) a power supply; and c) a visualization means. In some embodiments, the microfluidic device is constructed of polydimethylsiloxane (PDMS), polymers, paper, or glass. In some embodiments, the system further comprises a data acquisition and storage component. In some embodiments, the data is telemeter data.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1A-B shows the Ti—Au—Ti electrodeformation chip with the bright field microscopy image of the triangular tip designed microelectrodes in the insert. (B) Schematic diagram of the experimental setup for electrodeformation-based platelet stiffness measurement.

FIG. 2A-E shows simulated electric field strength in parallel (A), castellated (B) and triangular (C) microelectrode array geometries. (D&E) Enlargement of the major cell trapping regions on castellated (D) and triangular (E) designs to emphasize the cell-trapping patterns between two electrodes.

FIG. 3A-B shows (A) Simulated Clausius-Mossotti (CM) factors as a function of AC field frequencies for human platelets suspended in different buffers. (B) Experimental platelet electrodeformation dependence against AC field frequencies.

FIG. 4A-B shows (A) Platelet electrodeformation dependence versus applied electric field strength at 1 MHz applied frequency. The averaged deformation of untreated (control, n=13) and 0.4% paraformaldehyde treated platelets (n=20) are plotted with diamond and square symbols, respectively, error bars indicate standard errors. The power fitted curve is shown as a black solid line. (B) Fluorescence image sequence demonstrating a single platelet deformed via a positive dielectrophoresis force generated by 0, 45, 75 and 90 $V_{pk-pk}$ applied AC voltages. Lengths of the platelet were measured along the axis of maximum deformation (labeled by white solid line) and labeled by text. The frequency of the AC electric field was 1 MHz.

FIG. 5A-C shows (A) Simulated electric field norm (pseudo color surface), electric potential distribution (colored contour line) and time averaged Maxwell surface stress tensor (red arrow) across a pair of microelectrodes. (B) Table of calculated time averaged horizontal electromagnetic force (along x-direction of figure A) applied to a single platelet under varying electric field strength. The frequency of the AC electric field was assumed as 1 MHz. (C) Stress-strain curves of untreated control (solid diamond) and 0.4% paraformaldehyde treated samples (solid circle); dotted lines are the linear fitted curves (In C: n=13 for control and n=20 for 0.4% PFA, error: standard error)

FIG. 6A-B shows the effect of electrodeformation on platelet activation. (A) P-selectin expression levels for untreated (control), electrodeformed and thrombin (0.125 µM) treated (positive control) platelets were quantified via fluorescence. (B) Fluorescence image of electrodeformed platelets. No significant morphologic evidence of activation was detected.

DETAILED DESCRIPTION

Provided herein are systems and methods for measuring mechanical properties of cell or cell component or fragments. In particular, provided herein are microelectrode configuration and systems for measuring platelet deformation and stiffness.

Provided herein are systems and method for measuring mechanical properties such as stiffness of cells (e.g., platelets, white blood cells (WBC), red blood cells (RBC); cellular elements (e.g., organelles such as mitochondria, lysosomes and the like; cellular fragments or other components; or budded, vesiculated, vacuolated or membranes containing cellular constitutents)). In particular, provided herein are microelectrodes for measuring platelet deformation. Notably the present invention measures mechanical properties of free floating, suspended or otherwise non-adherent cells.

Recent work by has demonstrated that modulation of platelet membrane fluidity limits platelet activation resulting from mechanical deformation and shear (Yamaguchi, J., et al., *Desensitization of DMSO-treated platelets to common agonists via membrane modulation.* Faseb Journal, 2014. 28(1); Tran, P. L. V., L.; Yamaguchi, J.; Brengle, W.; DeCook, T. E.; Hutchinson, M.; Sen, N.; Bluestein, D.; Slepian, M. J. *Dimethyl Sulfoxide: A New Nemesis of Shear-Induced Platelet Activation.* in *Nanoengineering for Medicine and Biology*. Feb. 2-5, 2014. San Francisco, Calif.). It has been also reported that modulation of membrane fluidity may alter cell stiffness (Haghi, M. T., D.; Wood, L. G.; Oliver, B.; Young, P. M.; Chrzanowski, W., *A "soft spot" for drug transport: modulation of cell stiffness using fatty acids and its impact on drug transport in lung model.* Journal of Materials Chemistry B, 2015. 3: p. 2583-2589; Sun, M., et al., *The effect of cellular cholesterol on membrane-cytoskeleton adhesion.* J Cell Sci, 2007. 120(Pt 13): p. 2223-31). Further recent studies have stated that stiffness alone, as an intrinsic material property of cells or cellular constituents may be an important variable in reactivity and responsiveness of the cell or element to exogenous mechanical forces. As such, modulation of platelet stiffness may provide a new means for therapeutically altering the responsiveness of platelets to mechanical deformation and shear. In order to pursue this approach, and further develop agents of clinical value, a methodology is needed to accurately and non-destructively measure platelet stiffness.

Several methods have been described to measure single cell stiffness (Van Vliet, K. J., G. Bao, and S. Suresh, *The biomechanics toolbox: experimental approaches for living cells and biomolecules.* Acta Materialia, 2003. 51(19): p. 5881-5905; Lim, C. T., E. H. Zhou, and S. T. Quek, *Mechanical models for living cells-A review.* Journal of Biomechanics, 2006. 39(2): p. 195-216) including: atomic force microscopy (AFM), molecular force spectroscopy, cytoindenter, flow cytometry, magnetic twisting cytometry, micropipette aspiration, microfluidics, magnetic tweezers, microplate manipulation, optical tweezers, microelectrodes (Burt, J. P. H., R. Pethig, and M. S. Talary, *Microelectrode devices for manipulating and analysing bioparticles*. Transactions of the Institute of Measurement and Control, 1998. 20(2): p. 82-90) and optical stretchers. In general these methods either require adhesion or fixation of the cell followed by some means of applied deformation—e.g. micropipette aspiration and optical tweezers (Guo, Q., S. Park, and H. S. Ma, *Microfluidic micropipette aspiration for measuring the deformability of single cells*. Lab on a Chip, 2012. 12(15): p. 2687-2695; Neuman, K. C. and A. Nagy, *Single-molecule force spectroscopy: optical tweezers, magnetic tweezers and atomic force microscopy*. Nature Methods, 2008. 5(6): p. 491-505), direct contact and deformation of cells and their surface—e.g. AFM and cytoindenter (Neuman et al., supra; Koay, E. J., A. C. Shieh, and K. A. Athanasiou, *Creep indentation of single cells*. Journal of Biomechanical Engineering-Transactions of the Asme, 2003. 125(3): p. 334-341), or altered flow or passage through constrictive channels or orifices leading to applied deformation and shear—e.g. microfluidics and flow cytometry (Lincoln, B., et al., *Deformability-based flow cytometry*. Cytometry Part A, 2004. 59A(2): p. 203-209; Hou, H. W., et al., *Deformability based cell margination-A simple microfluidic design for malarial infected red blood cell filtration*. 6th World Congress of Biomechanics (Wcb 2010), Pts 1-3, 2010. 31: p. 1671-1674). These methods are best suited to measure the mechanical properties of adherent, anchorage-dependent cells e.g. fibroblasts or epithelial cells; or for free-floating, anchorage-independent, suspended cells that are have limited shear sensitivity—e.g. lymphocytes or circulating tumor cells. As such, they are poorly suited to measure the stiffness of un-activated resting platelets due to their free floating nature, extreme sensitivity to activation upon significant attachment or tethering to a foreign surface, and sensitivity to shear and applied force as a means of activation. Similarly, this concept applies to other free floating cells—e.g. WBCs, RBCs, circulating tumor cells, circulating progenitor stem cells—e.g. endothelial progenitor cells (EPCs). See also, U.S. Pat. Nos. 9,250,113; 9,074,978; 8,771,933; 9,134,294; 8,935,098; 8,771,933; 8,499,645; and 7,553,662. Hence an opportunity and need exists for development of a simple method capable of measuring stiffness of suspended, un-activated cells—e.g., platelets, that is free from significant cell surface area contact, requirement for surface adhesion or significant applied shear or direct deformation.

Dielectrophoresis (DEP) is a technique in which neutral particles are polarized when subjected to a non-uniform electric field, leading to translational motion of the particles, e.g. their attraction or repulsion (Pohl, H. A., *Dielectrophoresis: the behavior of neutral matter in nonuniform electric fields* Vol. 80. 1978: Cambridge university press Cambridge; Bakewell, D. V.-I., N.; Holmes, D., *Dielectrophoresis of Biomolecules*. JSM Nanotechnology & Nanomedicine, 2013. 1(1003): p. 1-14; Pohl, H. A., *The Motion and Precipitation of Suspensoids in Divergent Electric Fields*. Journal of Applied Physics, 1951. 22(7): p. 869-871). DEP has been applied to cells and has proven effective as a means of inducing movement that has been utilized for cell separation and partitioning (Pohl, H. A. and J. S. Crane, *Dielectrophoresis of Cells*. Biophysical Journal, 1971. 11(9): p. 711; Hu, X. Y., et al., *Marker-specific sorting of rare cells using dielectrophoresis*. Proceedings of the National Academy of Sciences of the United States of America, 2005. 102(44): p. 15757-15761; Pohl, H. A., *Dielectrophoresis: Applications to the Characterization and Separation of Cells, in Methods of Cell Separation*, N. Catsimpoolas, Editor. 1977: New York.). Further, DEP has been utilized as a cell characterization tool to measure cell electrical properties (26-28; Pohl, H. A. and I. Hawk, *Separation of living and dead cells by dielectrophoresis*. Science, 1966. 152 (3722): p. 647). To date, DEP has not been utilized as dynamic means to modulate a cell, cell component or fragment, and by virtue of that response—e.g., elongation or shortening, derive a mechanical property. Further that approach has not been utilized for free floating cells—e.g., platelets and white cells or cell components or fragments. That novelty is herein described in the present invention. No studies have examined the utilization of this approach for platelets.

Experiments described herein demonstrate the use of dielectrophoresis as a means of trapping and stabilizing individual, free-floating, resting platelets and subjecting them to electrodeformational forces. Further, by varying the field strength of the electrodeformational force, coupled with measurement of the extent of cell deformation, the overall stiffness of the platelet can be determined. The present method provides advantage in that cells are suspended and deformation occurs without full anchoring. As such stiffness is determined without contact of an external probe or test device, with minimal contact (e.g., <1.25%), of the platelet surface area. This is of particular value for platelets, which are contact sensitive, for which mild mechanical perturbation above a threshold leads to activation, with shape change and initiation of thrombosis.

To characterize platelet stiffness quantitatively, the described methodology was used to calculate Youngs' modulus. Platelet Young's modulus was derived from the measured deformation—stress relationship. Tensile stresses applied to platelet surfaces were calculated by mathematical simulation using the Maxwell stress tensor integration method (FIG. 5B). Extension deformations were experimentally measured (FIG. 5C). The result estimated that the Young's modulus of resting platelets was between 3.5+/−1.4 kPa corresponding to Young's modulus determination as was previously reported (Haga, J. H., et al., *Quantification of the passive mechanical properties of the resting platelet*. Ann Biomed Eng, 1998. 26(2): p. 268-77). Although not directly comparable, the Young's modulus of activated platelets measured by AFM method was reported to be between 100-5000 Pa depending upon the measurement location (Radmacher, M., et al., *Measuring the viscoelastic properties of human platelets with the atomic force microscope*. Biophys J, 1996. 70(1): p. 556-67).

Recently a multiscale modeling approach was used to study the effects of platelet deformability on flowing platelet hemodynamics and its resulting membrane dynamic shear stress distribution that may induce platelet activation (Zhang, P., et al., *Multiscale Particle-Based Modeling of Flowing Platelets in Blood Plasma Using Dissipative Particle Dynamics and Coarse Grained Molecular Dynamics*. Cellular and Molecular Bioengineering, 2014. 7(4): p. 552-574). Rigidity, usually applied in platelets simulations because of their much higher stiffness as compared to RBCs, is likely to lead to an overestimation of their activation potential. By comparing rigid and deformable platelets simulated while flipping in Couette shear flow, it was demonstrated that deformability significantly influences the flow-induced shear stress levels on the platelet membranes. The stresses in the rigid model were approx. 2.6 times higher as compared to the deformable model (Zhang et al., supra). By removing the rigidity constraint for simulating mechanotransduction processes this model offers description of processes where, e.g., membrane stiffening plays a role (Martinez, E. J., Y. Lanir, and S. Einav, *Effects of contact-induced membrane stiffening on platelet adhesion*. Biomech Model Mechanobiol, 2004. 2(3): p. 157-67; Ward, M. D. and D. A. Hammer, *A theoretical analysis for the effect of focal contact formation on cell-substrate attachment strength*. Biophys J, 1993. 64(3): p. 936-59; Avrahami, I. and M. Gharib. *Effects of membrane stiffening on focal-adhesion bonding under steady and unsteady conditions*. in *Bio Micro and Nanosystems Conference*, 2006. BMN'06. 2006. IEEE; Pasqua, A., et al., *Large-scale simulations of fluctuating biological membranes*. Journal of Chemical Physics, 2010. 132(15): p. 15410) such as membrane flexibility loss during adhesion because of the stiffening (Martinez et al., supra; Avrahami et al., supra). The electrodeformation approach for measuring platelets stiffness in vitro will be further applied by us for validating the numerical predictions. It will also be applied to studies examining manipulation of platelet membrane fluidity and flexibility by pharmacological agents, as are presently ongoing (Tran, P. L., Valerio, L., Yamaguchi, J., Brengle, W., DeCook, T. E., Hutchinson, M., Sen, N., Bluestein, D., Slepian, M. J. *Dimethyl Sulfoxide: A New Nemesis of Shear Induced Platelet Activation*. in *Nanoengineering for Medicine and Biology*. 2014. San Francisco, Calif.).

Finally, a distinguishing feature of the DEP electrodeformation method is the lack of platelet activation observed. While there are reports in the literature that nanosecond pulse electric fields can activate platelets (Zhang, J., et al., *Nanosecond pulse electric field (nanopulse): a novel non-ligand agonist for platelet activation*. Arch Biochem Biophys, 2008. 471(2): p. 240-8), at the levels utilized by the method no morphological changes in platelets, before and after electrodeformation, were observed (FIG. 6B). Compared to platelets activated by the commonly known agonist, thrombin, platelet activation induced by electrodeformation was insignificant (FIG. 6A).

In summary, dielectrophoresis-induced electrodeformation applied to platelets via specifically designed, triangular, single point microelectrode chips allowed for successful trapping and cyclic deformation of platelets. Applying a range of field strengths to trapped cells allowed for a range of deformations to be obtained, which can be captured and quantified for stiffness determination. Over the range of electric fields utilized no significant degree of platelet activation was detected. Utilizing the Maxwell stress tensor integration method applied force was calculated and individual platelet stiffness determined from the stress-deformation relationship derived. The present method extends tools available for cell biology research and for studies of platelet mechano-transduction, as a technique that is free from confounding effects associated with significant cell contact, underlying substrate effects or repeated contact-mediated damage.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "conventional" designates that which is known in the prior art to which this technology relates.

As used herein, the term "means for a function" indicates that the scope of the technology encompasses all means for performing the function that are described herein and all other means commonly known in the art at the time of filing.

As used herein, the terms "animal", "subject", and "patient" specifically include mammals, such as a human, as well as cattle, horses, dogs, cats, and birds, but also can include many other species having a cardiovascular system.

As used herein, a "therapeutic agent" is a drug, pharmaceutical, etc., and may be, e.g., an agent that changes viscosity or membrane properties of platelets. A therapeutic agent may be a nutraceutical or a food.

Description

Although the disclosure herein refers to certain illustrated embodiments, it is to be understood that these embodiments are presented by way of example and not by way of limitation.

Embodiments of the present disclosure provide compositions and methods for measuring mechanical properties of cell (e.g., platelet), cell fragment, or cell components. In some embodiments, systems and methods utilize a microelectrode chip comprising a plurality of parallel microelectrodes (e.g., arranged in a triangular tip orientation). Electrical current is applied (e.g., via a power supply), trapping platelets in the current. Platelet are then stained and visualized (e.g., using a microscope). Deformation is then measured (e.g., manually or using an automated analysis system) and correlated with platelet stiffness. In some embodiments, increased or decreased platelet stiffness is correlated with decreased or increased platelet activity.

The systems and methods described herein find use in a variety of research, diagnostic, and screening applications. For example, in some embodiments, the systems and methods described herein find use in drug screening applications (e.g., to assay the effect of test compounds on platelet activity). Exemplary embodiments are described herein.

Testing

In some embodiments, a subject is tested to assess cell (e.g., platelet) stiffness using the systems and methods described herein. In some embodiments, platelets are contacted with a test compound (e.g., drug) or research reagent prior to measuring stiffness. In some embodiments, platelets from a patient are tested for stiffness, a patient is treated for a disease or condition, and platelet stiffness is assay again. In some embodiments, cycles of testing and treatment occur without limitation to the pattern of testing and treating (e.g., test/treat, test/treat/test, test/treat/test/treat, test/treat/test/treat/test, test/treat/treat/test/treat/treat, etc), the periodicity, or the duration of the interval between each testing and treatment phase.

Reproducing Device Shear Stress in a Microfluidic Device

Embodiments of the technology relate to emulating the individual shear and flow characteristics (e.g., defined flight trajectories) of a given MCS device or a cardiovascular pathology in a microfluidic channel system. In particular, embodiments of the technology are related to a small point-of-care system comprising a "device specific" microfluidic facsimile for assessing anti-thrombotic drug activity in a patient. During the development of embodiments of the technology, experiments were conducted to test using microfluidic technologies to replicate the flow-related thrombogenic potential of MCSs. In particular, the geometry of microfluidic devices is designed to replicate a device-specific or pathology-specific shear stress curve based on the stress models previously determined for that device. Embodiments of the microfluidic devices provided herein provide advantages that expand the potential applications of this technology. For example, microfluidic tests require small samples (e.g., a small volume of blood), thus providing embodiments of methods for monitoring patient blood susceptibility and/or the effect of drug therapy frequently and on a routine basis.

Microfluidic Devices

Embodiments of the present invention utilize microfluidic devices. Microfluidic technologies provide many advantages (see, e.g., S. R. Quake and A. Scherer, "From Micro to Nano Fabrication with Soft Materials," Science, vol. 290, pp. 1536-40, 2000). Generally, microfluidic devices handle small amounts of fluids, e.g., having volumes of 1-1000 µL, 1-1000 nL, 1-1000 pL, or 1-1000 fL. Microfluidic devices typically have a small size and consume small amounts of reagents and energy. Finally, advantages of the technology are related to the behavior of small volumes of fluids with the microstructures of a microfluidic device. See, e.g., Squires and Quake (2005), "Microfluidics: Fluid physics at the nanoliter scale". Reviews of Modern Physics 77: 977, incorporated herein by reference in its entirety.

For example, microfluidic technologies provide for testing a sample having a small volume (e.g., $10^{-9}$ to $10^{-18}$ liters), thus minimizing or eliminating patient discomfort (e.g., from acquiring blood samples having reduced volume) and reducing the quantities and related costs of reagents, compounds, and pharmaceuticals that are associated with clinical tests. Further, the high surface-to-volume ratio of microfluidic devices dramatically reduces reaction times. Moreover, microfluidic devices provide for precise fluid handling. And, finally, microfluidics allows one to manipulate and to run parallel tests on a single small device.

In some embodiments of the technology provided herein, microfabrication techniques are used to produce a microfluidic device. For example, in some embodiments a microfluidic device is produced by a method comprising replica molding using soft lithography methods. In some embodiments, replica molding using soft lithography comprises producing microfluidic platforms from polydimethylsiloxane (PDMS). PDMS is a silicon rubber that provides advantages related to fabrication, physical properties, and economy (see, e.g., J. Friend and L. Yeo. "Fabrication of microfluidic devices using polydimethylsiloxane," Biomicrofluidics, vol. 4, pp: 026502, 2010). PDMS microfluidic platforms have further advantages related to transparency, gas permeability, and chemical stability (e.g., chemical inertness).

In various embodiments, microfluidic devices are fabricated from various materials using techniques such as laser stenciling, embossing, stamping, injection molding, masking, etching, and three-dimensional soft lithography. Laminated microfluidic devices are further fabricated with adhesive interlayers or by thermal adhesiveless bonding techniques, such as by pressure treatment of oriented polypropylene. The microarchitecture of laminated and molded microfluidic devices can differ.

In some embodiments, microchannels are constructed of layers formed by extrusion molding. The flow characteristics of microchannels are significant because of the surface effects in the microflow regime. Surface tension and viscosity influence (e.g., enhance) surface roughness effects. In some embodiments, the narrowest dimension of a channel has the most profound effect on flow. Flow in channels that have rectangular or circular cross-sectional profiles is controlled by the diagonal width or diameter; thus, in some embodiments, channel design is typically varied to take advantage of this behavior. In some embodiments, reduction of taper in the direction of flow leads to a wicking effect for diameters below 200 micrometers. Conversely, flow can be stopped by opening a channel to form a bulb; then, flow can be restored by applying a pressure. Vias in a channel can be designed to promote directional flow, e.g., to provide a type of solid-state check valve.

In some embodiments, microfluidic devices described herein are fabricated from an elastomeric polymer such as, e.g., polyisoprene, polybutadiene, polychlorophene, polyisobutylene, poly(styrene-butadiene-styrene), nitriles, polyurethanes, or polysilicones. In some embodiments, GE RTV 615, a vinyl-silane crosslinked (type) silicone elastomer (family) or polydimethysiloxane (PDMS) (e.g., sold as HT-6135 and HT-6240 from Bisco Silicons, Elk Grove, Ill.) is useful. The choice of materials typically depends upon the particular material properties (e.g., solvent resistance, stiffness, gas permeability, and/or temperature stability) required for the application being conducted. In some embodiments, elastomeric materials that are used in the manufacture of components of the microfluidic devices are described in Unger (2000) Science 288:113-116, incorporated herein by reference in its entirety. Some elastomers of the present devices are used as diaphragms. In some embodiments, elastomers are selected for their porosity, impermeability, chemical resistance, wetting, and passivating characteristics in addition to their stretch and relax properties. In some embodiments, an elastomer is selected for its thermal conductivity. For example, Micrometrics Parker Chomerics Therm A Gap material 61-02-0404-F574 (0.020" thick) is a soft elastomer (<5 Shore A) needing only a pressure of 5 to 10 psi to provide a thermal conductivity of 1.6 W/m-K.

Computer and Software

In some embodiments, the technology described herein is associated with a programmable machine designed to perform a sequence of arithmetic or logical operations, e.g., as provided by the methods described herein, either contiguous to the device, proximate, or utilized in concert. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a processor or a microprocessor) for executing a series of instructions (e.g., a method as provided herein) to read, manipulate, and store data. Some embodiments comprise one or more processors. In some embodiments, a processor provides instructions to control one or more components of the system (e.g., voltage applied to the microelectrode).

In some embodiments, a microprocessor is part of a system comprising one or more of a CPU, a graphics card, a user interface (e.g., comprising an output device such as a display and an input device such as a keyboard), a storage medium, and memory components. Memory components (e.g., volatile and/or nonvolatile memory) find use in storing instructions (e.g., an embodiment of a process as provided herein) and/or data. Programmable machines associated with the technology comprise conventional extant technologies and technologies in development or yet to be developed (e.g., a quantum computer, a chemical computer, a DNA computer, an optical computer, a spintronics based computer, etc.).

Some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor, such as the processor of client, with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C #, Visual Basic, Java, Python, Perl, Swift, Ruby, Unix, and JavaScript.

Computers are connected in some embodiments to a network or, in some embodiments, can be stand-alone machines. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computer-related to aspects of the technology provided herein may be any type of processor-based platform that operates on any operating system, such as Microsoft Windows, Linux, UNIX, Mac OS X, etc., capable of supporting one or more programs comprising the technology provided herein. All such components, computers, and systems described herein as associated with the technology may be logical or virtual.

Data Collection and Analysis

In some embodiments, assay data are produced. Following the production of assay data, the assay data are reported to a data analysis operation in some embodiments. Data may be stored on the device, telemetered to a proximate data storage means or at a distance via bluetooth or other contained transmission means or via connectivity to the worldwide web. To facilitate data analysis in some embodiments, the assay data are analyzed by a digital computer. In some embodiments, the computer is appropriately programmed for receipt and storage of the assay data and for analysis and reporting of the assay data gathered, e.g., to provide a drug dosage, or platelet stiffness report in a human or machine readable format.

In some embodiments, a computer-based analysis program is used to translate the data generated by an assay (e.g., platelet stiffness) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to utilize the information immediately to optimize the care of the subject. The present invention contemplates any method capable of receiving, processing, and transmitting the information to and from laboratories conducting the assays, information providers, medical personal, and subjects.

EXAMPLES

Example 1

Materials and Methods

Platelet Isolation

Gel filtered platelets were prepared as previously described, from whole blood drawn from aspirin and non-steroidal anti-inflammatory medication free volunteers providing informed consent (Sheriff, J., et al., High-shear stress sensitizes platelets to subsequent low-shear conditions. Ann Biomed Eng, 2010. 38(4): p. 1442-50).

Microelectrode Chip Fabrication

Parallel microelectrodes with gap separations of 10 µm, (FIG. 1(A)), were fabricated on a glass substrate by a lift-off process. A series of 500 Å titanium (Ti), 1500 Å gold and 500 Å Ti metal thin film were deposited onto a photoresist-patterned substrate by sputtering before resist development. A 127 µm-thick hollow polymer spacer was placed on top of the chip to create a fluid chamber and the chip was covered with a coverslip for microscopic observation. All chip glass surfaces were coated with Sigmacote (Sigma-Aldrich, MO, USA) and rinsed with D.I. water to prevent surface-induced platelet activation.

Electrodeformation Assay

To visualize platelets they were first exposed to Alexa Fluor 594 conjugated wheat germ agglutinin (1 µg/mL, 10 mins, 37° C., Invitrogen, CA). Platelets were then diluted 100-200 fold (v/v) in isotonic buffer (Pommer, M. S., et al., *Dielectrophoretic separation of platelets from diluted whole blood in microfluidic channels*. Electrophoresis, 2008. 29(6): p. 1213-8) containing 8.5% w/v sucrose and 0.3% w/v dextrose until the medium conductivity reached ~1500/cm. as measured by a Jenway 4520 conductivity meter (Jenway, Staffordshire, UK). 50 µl of the diluted platelets sample were pipetted into the fluid chamber of the microelectrode chip. An alternating electric current in a sine wave pattern was generated across the microelectrodes using a function generator (332220A, Agilent, CA,) connected to a wideband power amplifier (7600M, Krohn-hite, MA). The amplitude of applied voltage was monitor via digital oscilloscope (GDS-1102, GW Instek, CA). The sample chip was imaged via fluorescence microscopy (Eclipse E800, 100× oil, Nikon, N.Y.), images were captured via CCD (Sensicam 12bt CCD camera, Cooke Corporation, MI), processed and quantified using NIH Image J software. The experimental setup for electrodeformation is schematically outlined in FIG. 1(B).

Platelet Activation Assay

Platelet activation level was quantified via cell surface expression of P-selectin utilizing immunohistochemical staining (Hsulin, S. C., et al., *A Platelet Membrane-Protein Expressed during Platelet Activation and Secretion-Studies Using a Monoclonal Antibody Specific for Thrombin-Activated Platelets*. Journal of Biological Chemistry, 1984. 259(14): p. 9121-9126; Berman, C. L., et al., *A Platelet Alpha Granule Membrane-Protein That Is Associated with the Plasma-Membrane after Activation-Characterization and Subcellular-Localization of Platelet Activation Dependent Granule-External Membrane-Protein*. Journal of Clinical Investigation, 1986. 78(1): p. 130-137; Berger, G., D. W. Hartwell, and D. D. Wagner, P-Selectin and platelet clearance. Blood, 1998. 92(11): p. 4446-52). Platelets were paraformaldehyde fixed (3%, 20 mins) rinsed and incubated (30 min., 37° C.) with FITC Mouse Anti-Human CD62P (50 µl, 1:5 (v/v) dilution in PBS, BD Biosciences, CA) and imaged using fluorescence microscopy. Fluorescence intensity levels were measured following background subtraction. Mean and standard error were averaged for >70 platelets under each experimental condition. Platelets incubated with 0.125 µM thrombin (10 mins, 37° C.) and untreated platelets served as positive and negative controls. Activation of the positive and negative controls was also quantified via the chemically modified prothrombin-based platelet activation state (PAS) assay (Jesty, J. and D. Bluestein, *Acetylated prothrombin as a substrate in the measurement of the procoagulant activity of platelets: Elimination of the feedback activation of platelets by thrombin*. Analytical Biochemistry, 1999. 272(1): p. 64-70.).

Mathematical Modeling

Mathematical modeling of the frequency dependency of the real part of the Clausius-Mossotti factor (Morgan, H., M. P. Hughes, and N. G. Green, *Separation of submicron bioparticles by dielectrophoresis*. Biophys J, 1999. 77(1): p. 516-25) was simulated by Matlab using parameters from the literature, listed in Table 1. The Clausius-Mossotti (CM) factor was defined by:

$$K(\omega) = \frac{\hat{\varepsilon}_c - \hat{\varepsilon}_m}{\hat{\varepsilon}_c + 2\hat{\varepsilon}_m}$$

where $\varepsilon_c$ and $\varepsilon_m$ are the relative permittivity of platelet cytoplasm and membrane. 2D mathematical modeling of the electrodynamic force, generated by non-uniform electric field, exerted on a single platelet surface was simulated by finite element analysis software, Comsol Multiphysics 4.4 (Comsol, Burlington, Mass.). The platelet was assumed as a linear, isotropic and lossy dielectric single shell sphere trapped on an electrode tip and submersed in a lossy dielectric medium. Relative permittivity of lossy dielectric ($\hat{\varepsilon}$) was defined as:

$$\hat{\varepsilon} = \varepsilon' + i\frac{\sigma}{\omega}$$

where $\varepsilon'$ is the real part of permittivity, $\sigma$ is the electric conductivity and $\omega$ is the angular frequency. Electric field induced electromechanical properties were governed by the Maxwell equation:

$$\nabla \times H = \sigma E + j\omega D + J_e$$

with the boundaries condition on cell-medium interface of:

$$n \cdot (J_1 - J_2) = -\nabla_t \cdot d_m((\sigma_m + j\varepsilon_0\varepsilon_m E)\nabla_t V)$$

The magnetic field intensity (H) was assumed as zero in the calculation. Electric field intensity (E) and displacement (D) are calculated by the gradient of potential (V):

$$E = -\nabla V$$

$$D = \varepsilon_0 \varepsilon_r E$$

where $\varepsilon_r$, $\varepsilon_0$ and $\varepsilon_m$ is the relative permittivity of the medium, vacuum and platelet membrane respectively, $\sigma_m$ is the electric conductivity of cell membrane, $d_m$ is membrane thickness, $J_1$ and $J_2$ are current density of internal and external boundaries, t is time, $J_e$ is the external source current density and n is vector normal to surface (S).

Electrodynamic force (F) applied on the cell surface can be estimated by integrating the Maxwells's stress tensor (T) over the cell surface, given by:

$$F = d\int_{\partial\Omega} n \cdot T dS$$

and $$T = \begin{bmatrix} \varepsilon_0\varepsilon_r E_x^2 - \frac{1}{2}\varepsilon_0\varepsilon_r(E_x^2 + E_y^2) & \varepsilon_0\varepsilon_r E_x E_y \\ \varepsilon_0\varepsilon_r E_x E_y & \varepsilon_0\varepsilon_r E_y^2 - \frac{1}{2}\varepsilon_0\varepsilon_r(E_x^2 + E_y^2) \end{bmatrix}$$

where $\Omega$ represent the cell body, d is the out-of-plane thickness, which assumed as the focal length of the microscope objective. (Chen, J., et al., *Electrodeformation for Single Cell Mechanical Characterization*. 2011 Ieee 24th International Conference on Micro Electro Mechanical Systems (Mems), 2011: p. 1119-1122).

Data Analysis

Student's t-test was performed to assess the statistical significance of the experimental results. Values statistically significant at $p<0.05$ were considered a difference.

Results

Microelectrode Chip Design and Fabrication

Microelectrode chip design was developed via a modification of a castellated (square indentations or turret-like) microelectrode array geometry (Wang, X. B., et al., Dielectrophoretic manipulation of particles. Ieee Transactions on Industry Applications, 1997. 33(3): p. 660-669; Ramos, A., et al., *Ac electrokinetics: a review of forces in microelectrode structures*. Journal of Physics D-Applied Physics, 1998. 31(18): p. 2338-2353). Under positive DEP, particles are trapped in the regions of the strongest electric field (Ramos et al., supra). As in FIG. 2, the triangular tip design (FIGS.

2c and 2e) enabled a more confined, single-point trapping position, compared to a castellated or parallel finger electrode layout (Zhang, C., et al., *Dielectrophoresis for manipulation of micro/nano particles in microfluidic systems.* Anal Bioanal Chem, 2010. 396(1): p. 401-20). This allowed more ready observation of single cell behavior, versus multiple cell trapping more likely with castellated or finger-like designs (FIGS. 2b and 2d). One important parameter to achieve trapping is the magnitude of electric field, defined as the potential difference against separation distance across electrodes. Microelectrodes with gap distances of 10 µm were tested to provide sufficient field strength for trapping and deforming platelets under a potential of 90-150$V_{pk\text{-}pk}$. To withstand such high input voltages, a titanium-gold-titanium (Ti—Au—Ti) sandwich structure was utilized to fabricate the chip. Titanium has relatively lower thermal conductivity and better biocompatibility (Lee, S. W., et al., *Development of microelectrode arrays for artificial retinal implants using liquid crystal polymers.* Invest Ophthalmol Vis Sci, 2009. 50(12): p. 5859-66) compared to most metals. Moreover, a thin layer of titanium dioxide film formed on top of the microelectrode helped prevent bubble formation or deterioration of the electrode from high voltages (Gao, J., et al., *Hybrid electrokinetic manipulation in high-conductivity media.* Lab on a Chip, 2011. 11(10): p. 1770-1775). However, as titanium has a comparably low electrical conductivity against other metals, a gold layer was embedded as the middle layer to oppose this drawback. The designed construct could be readily and reproducibly fabricated.

Dielectrophoresis-Mediated Platelet Trapping

Dielectrophoresis imparted via the fabricated microelectrode chips was found to readily and reliably capture and trap platelets. Capture of platelets on microelectrode tip edges was observed when a gradually increasing AC voltage from 90-150$V_{pk\text{-}pk}$ at 1 MHz was applied. Theoretically, DEP is a lateral motion generated on uncharged particles due to polarization induced by non-uniform electric field (Leung, S. L., et al., *Gold nano-particle-based thermal sensors fabricated using microspotting and DEP techniques.* Sensors and Actuators a-Physical, 2012. 178: p. 32-39). The time averaged DEP force exerted on platelets was obtained by:

$$<F_{DEP}(t)> = 2\pi\varepsilon_r a^3 \text{Re}[K(\omega)]\nabla|E_{rms}|^2$$

where $|E_{rms}|^2$ is the time-averaged root-mean-square magnitude of electric field intensity and $\text{Re}[K(\omega)]$ is the real part of Clausius-Mossotti (CM) factor, which determines the magnitude and direction of DEP force.

Real CM factors of platelets in DI water, isotonic buffer, electrodeformation buffer (diluted platelet buffer in isotonic buffer) and platelet buffer were simulated in FIG. 3A using parameters from the literature, listed in Table 1. The imaginary relative permittivity of medium and cytoplasm was neglected in this calculation. The simulations predicted positive DEP forces would be generated at frequency ranges of 1 k-10 MHz for DI water, 7 k-10 MHz for isotonic buffer and 20 k-20 MHz for electrodeformation buffer. Conversely, only a negative DEP force would be generated in platelet buffer under an applied frequency of 1 k-1 GHz. Further, the simulations predicted that adequate deformation would occur with only minimal cell contact with the electrode tip. As such, with an electrode tip contact area of 0.25 µm$^2$, based on a generally rectangular tip configuration, with dimensions of 0.25 µm (height)×1 µm (width), and an average platelet surface area of 20-30 µm$^2$ (Sims, P. J., et al., *Complement proteins C5b-9 cause release of membrane vesicles from the platelet surface that are enriched in the membrane receptor for coagulation factor Va and express prothrombinase activity.* J Biol Chem, 1988. 263(34): p. 18205-12.), only 0.83-1.25% of the platelet surface area is significantly engaged utilizing this methodology.

Frequency Dependence of DEP-Mediated Electrodeformation

In frequency dependency studies, an applied voltage of 90$V_{pk\text{-}pk}$ was utilized to deform trapped platelets. Applied frequencies were maintained higher than 0.5 MHz to avoid electrolysis, which had been observed at frequencies lower than 0.5 MHz. Platelet deformation along the axis of maximum extension was measured and normalized based on the original length. As shown in FIG. 3B, a decrease in deformation from 12.7±7.52% to −0.8±3.6% was observed when the applied frequency increased from 0.5 MHz to 10 MHz. Compare to the stimulated CM factor, shown in FIG. 3A, the frequency range of the positive DEP force was well predicted without any fitting parameters.

Voltage Dependence of Electrodeformation

According to the theory of dielectrophoresis, the magnitude of the DEP force is proportional to the square of the applied voltages. In the studies, platelet deformations under sequential increase of applied voltage, from 0 to 90$V_{pk\text{-}pk}$ at 15V steps, were measured at a frequency of 1 MHz and the result is shown in FIG. 4A. Rapid deformations were observed immediately following application of voltage oscillations. Images of deformed platelets were captured in a duration ~5s. Representative images of a single platelet deformed by the increased magnitude of applied forces were demonstrated in FIG. 4B, showing reversible deformations of 7, 10 and 16% at applied voltages of 45, 75 and 90$V_{pk\text{-}pk}$ respectively. To verify that the measured deformations were dependent on platelet stiffness, a low concentration of cell fixative, i.e. 0.4% paraformaldehyde, was utilized to stiffen the platelets. The measured deformations were increased from 0.73±1.33% to 4.90±1.98% when applied voltages increased from 15 to 90V. Compared to untreated platelets, a significant drop in platelet deformation lengths was observed, with p-values <0.05. Deformation was decreased by 2.75 times at 90$V_{pk\text{-}pk}$ applied voltage, with p-value=0.0002.

Young's Modulus Simulation

A COMSOL Multiphysics 2D electric current model consisting of three parallel microelectrodes, with identical geometry to those of the experimental chips, was created for simulating the electrodynamic forces exerted on the platelet surface. The general method utilized for estimating the forces was by integrating the Maxwells's stress tensor over the cell surface (Chen, J., et al., *Electrodeformation for Single Cell Mechanical Characterization.* 2011 Ieee 24th International Conference on Micro Electro Mechanical Systems (Mems), 2011: p. 1119-1122; Wang, X. J., X. B. Wang, and P. R. C. Gascoyne, *General expressions for dielectrophoretic force and electrorotational torque derived using the Maxwell stress tensor method.* Journal of Electrostatics, 1997. 39(4): p. 277-295). Assuming the chip was grounded at the top and bottom edges while electric current was applied on the left and right, the electric parameters as listed in Table 1 and the out-of-plane thickness as 100 nm, approximately equaled to the focal length of the objective. The simulated results of electric field norm, electric potential distribution and time-averaged Maxwell surface tensor generated by a 90$V_{pk\text{-}pk}$ AC applied voltage at 1 MHz frequency was demonstrated in FIG. 5A.

By Maxwells's stress tensors integration, time-averaged electromagnetic force parallel to the microelectrode was calculated and listed in FIG. 5B. The magnitude of DEP forces increased by the square of electric field strength; from 0.125 to 4.5 nN when the applied voltage increased from 15 to 90$V_{pk-pk}$. Young's modulus (E), defined as the ratio of the stress ($\sigma$=F/A) to the amount of deformation ($\varepsilon$=$\Delta$L/L), of the platelets was obtained by the slope of linear fitted stress-deformation curve, shown in FIG. 5C. They were estimated be 3.5+/−1.4 kPa for resting platelets and 8.5+/−1.5 kPa for platelets treated by 0.4% paraformaldehyde. The measured deformations were compared to the simulated deformation calculated by the estimated Young's moduli. In both conditions, resting and 0.4% paraformaldehyde treated platelets, the $R^2$ value between the two curves were >0.97.

Platelet Activation Studies

It was next examined whether DEP-mediated electrodeformation would inadvertently activate platelets. As shown in FIG. 6A, P-selectin expression in thrombin-activated platelets was significantly higher than electrodeformed platelets and untreated platelets, with averaged fluorescence intensity levels of 1526.15±75.04 versus 309.04±26.79 and 238.89±21.64, respectively. The activation level of untreated and thrombin-activated platelets was verified via use of the PAS assay and resulted in <1% and 24.7% activation, respectively. Compared to platelets activated by a known agonist, no major activation of platelet was observed with DEP-induced electrodeformation as employed in the assay. To further investigate the effect of electrodeformation on platelet activation, the morphology of platelets before and after a cycle of voltage dependent deformation was compared, as shown in FIG. 6B. No observable morphological changes were detected. Pearson correlation coefficient between two images was calculated using the Image J Co-localization Finder Plugin with a result of 0.859, indicating a high correlation between the two images. As such, morphologically, no significant platelet activation was observed.

TABLE 1

List of electrical properties of platelets and electrodeformation buffer [37] [69]

| Parameters | Values |
| --- | --- |
| Real relative permittivity of medium, $\varepsilon'_r$ | 80 |
| Real relative permittivity of platelet membrane, $\varepsilon'_m$ | 10 |
| Relative permittivity of platelet cytoplasm, $\varepsilon_c$ | 40 |
| Electric conductivity of platelet membrane, $\sigma_m$ | 0.00001 S/m |
| Electric conductivity of platelet cytoplasm, $\sigma_c$ | 0.1 S/m |
| Radius of platelet | 2 µm |
| Platelet membrane thickness | 10 nm |

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method of measuring membrane stiffness, comprising:
    a) trapping a plurality of cells, cell membranes comprising cellular components, or cell components in microelectrodes of a system, comprising i) a microelectrode chip comprising at least two parallel microelectrodes arranged in a triangular tip orientation, wherein said microelectrodes are configured to deliver a varying electric field generated by dielectrophoresis to said cells, cell membranes comprising cellular components, or cell components; ii) a power supply; and iii) a visualization means;
    b) applying said varying electric field generated by dielectrophesis to said trapped cells to deform said cells; and
    c) measuring deformation of said cells, cell membranes comprising cellular components, or cell components in said electric field by measuring deformation of said cells, cell membranes comprising cellular components, or cell components along an axis of maximum extension and normalizing the deformation to an original length, wherein the magnitude of deformation of said cells, cell membranes comprising cellular components, or cell components is proportional to stiffness of said cells, cell membranes comprising cellular components, or cell components.

2. The method of claim 1, wherein said cell is a non-adherent cell.

3. The method of claim 1, wherein said cell is selected from the group consisting of platelets, white blood cells, red blood cells, circulating tumor cells, bone marrow cells, stem cells, progenitor cells, and endothelial progenitor cells.

4. The method of claim 1, wherein said cell components are selected from the group consisting of microparticles, mitochondria, golgi, lusosomes, and peroxisomes.

5. The method of claim 1, wherein said cell membranes comprising cellular components are selected from the group consisting of budded, vesiculated, vacuolated, or membrane-containing cellular constituents.

6. The method of claim 1, wherein said microelectrode chip further comprises a fluid chamber on top of said chip.

7. The method of claim 1, wherein said microelectrode has an electrode gap distance of approximately 10 µm.

8. The method of claim 1, wherein said microelectrodes have a surface coating of a Ti—Au—Ti sandwich.

9. The method of claim 1, wherein said visualization means is selected from the group consisting of a microscope, a camera, and a CCD device.

10. The method of claim 9, wherein said microscope is a bright field microscope.

11. The method of claim 1, wherein said cell is a platelet.

12. A method of measuring platelet stiffness, comprising:
    a) trapping a plurality of platelets in microelectrodes of a system, comprising i) a microelectrode chip comprising at least two parallel microelectrodes arranged in a triangular tip orientation, wherein said microelectrodes are configured to deliver a varying electric field generated by dielectrophoresis to said platelets without activating said platelets; ii) a power supply; and iii) a visualization means;
    b) applying said varying electric field generated by dielectrophesis to said trapped platelets to deform said cells; and
    c) measuring deformation of said platelets, in said electric field by measuring deformation of said platelets along an axis of maximum extension and normalizing the deformation to an original length, wherein the magnitude of deformation of said platelets proportional to stiffness of said platelets.

\* \* \* \* \*